(12) United States Patent
Trimble et al.

(10) Patent No.: US 11,771,607 B2
(45) Date of Patent: *Oct. 3, 2023

(54) PATIENT SUPPORT APPARATUS WITH DECK SECTION ACTUATOR

(71) Applicant: Stryker Corporation, Kalamazoo, MI (US)

(72) Inventors: Shawn Trimble, Portage, MI (US); Christopher S. Hough, Kalamazoo, MI (US); Bryan E. Garfoot, Portage, MI (US); Ross Timothy Lucas, Paw Paw, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/546,166

(22) Filed: Dec. 9, 2021

(65) Prior Publication Data

US 2022/0096298 A1 Mar. 31, 2022

Related U.S. Application Data

(63) Continuation of application No. 16/210,886, filed on Dec. 5, 2018, now Pat. No. 11,224,549.
(Continued)

(51) Int. Cl.
*A61G 7/018* (2006.01)
*A61G 7/10* (2006.01)
(Continued)

(52) U.S. Cl.
CPC .............. *A61G 7/018* (2013.01); *A61G 1/04* (2013.01); *A61G 7/0506* (2013.01); *A61G 7/07* (2013.01);
(Continued)

(58) Field of Classification Search
CPC ...... A61G 7/015; A61G 7/018; A61G 7/0509; A61G 7/012; A61G 1/04; A61G 7/0506;
(Continued)

(56) References Cited

U.S. PATENT DOCUMENTS

| 4,685,736 A | 8/1987 | Tanaka et al. |
| 5,590,932 A | 1/1997 | Olivieri |

(Continued)

FOREIGN PATENT DOCUMENTS

| WO | 2004021952 A2 | 3/2004 |
| WO | 2014020712 A1 | 2/2014 |
| WO | 2015032003 A1 | 3/2015 |

OTHER PUBLICATIONS

English language abstract for WO 2014/020712 extracted from espacenet.com database on Feb. 14, 2019, 2 pages.
(Continued)

*Primary Examiner* — David R Hare
*Assistant Examiner* — Madison Emanski
(74) *Attorney, Agent, or Firm* — Howard & Howard Attorneys PLLC

(57) ABSTRACT

A patient support apparatus for supporting a patient comprising a support frame and a support deck coupled to the support frame. The support deck has a deck section arranged to articulate relative to said support frame between a first position and a second position. An actuator is interposed in force-translating relation between the support frame and the deck section to articulate the deck section. The actuator comprises a biasing device configured to store mechanical energy and having an interface. The actuator further comprises a torque multiplier coupled to the deck section and engaged with the interface to translate mechanical energy stored in the biasing device into force acting on the deck section to urge the deck section toward the first position.

17 Claims, 13 Drawing Sheets

Related U.S. Application Data

(60) Provisional application No. 62/609,032, filed on Dec. 21, 2017.

(51) Int. Cl.

| | | |
|---|---|---|
| *A61G 7/05* | (2006.01) | |
| *A61G 1/04* | (2006.01) | |
| *A61G 7/07* | (2006.01) | |
| *A61G 7/08* | (2006.01) | |
| *A61B 5/00* | (2006.01) | |

(52) U.S. Cl.
CPC .............. *A61G 7/08* (2013.01); *A61G 7/1013* (2013.01); *A61B 5/6892* (2013.01); *A61B 2562/0252* (2013.01); *A61G 7/0528* (2016.11); *A61G 7/1046* (2013.01); *A61G 7/1067* (2013.01); *A61G 2203/32* (2013.01)

(58) Field of Classification Search
CPC .......... A61G 7/07; A61G 7/08; A61G 7/1013; A61G 7/0528; A61G 7/1046; A61G 7/1067; A61G 2203/32; A47C 1/025; A47C 1/026; A47C 20/041; A61B 2562/0252; F16H 1/46; F16H 2035/005
See application file for complete search history.

(56) References Cited

U.S. PATENT DOCUMENTS

| | | |
|---|---|---|
| 5,868,403 A | 2/1999 | Culp et al. |
| 6,145,930 A | 11/2000 | Su |
| 6,158,536 A | 12/2000 | Misawa |
| 6,648,343 B2 | 11/2003 | Way et al. |
| 6,739,004 B1 | 5/2004 | Abrahamsen et al. |
| 6,805,209 B2 | 10/2004 | Hedeen |
| 6,907,945 B2 | 6/2005 | Kim |
| 7,125,022 B2 | 10/2006 | Medina |
| 7,311,160 B2 | 12/2007 | Lim |
| 7,316,405 B2 | 1/2008 | Kritman et al. |
| 7,384,046 B2 | 6/2008 | Le Masne De Chermont |
| 7,434,815 B2 | 10/2008 | Kikusato |
| 7,520,347 B2 | 4/2009 | Chambliss et al. |
| 7,641,211 B2 | 1/2010 | Ivanchenko |
| 7,841,611 B2 | 11/2010 | Ivanchenko |
| 7,950,673 B2 | 5/2011 | Reed et al. |
| 7,980,337 B2 | 7/2011 | A/L Lynkaran et al. |
| 8,459,660 B2 | 6/2013 | Livingston |
| 11,224,549 B2 * | 1/2022 | Trimble .................. A61G 7/07 |
| 2004/0206555 A1 | 10/2004 | Schneider |
| 2006/0195987 A1 | 9/2006 | Walkingshaw |
| 2014/0115785 A1 | 5/2014 | Turner |
| 2014/0299391 A1 | 10/2014 | Carletti |
| 2017/0181908 A1 | 6/2017 | Jackson et al. |
| 2019/0192365 A1 | 6/2019 | Trimble et al. |

OTHER PUBLICATIONS

Hotrod, "Wpengine: How Gear Works—Car Craft Magazine", Hot Rod, www.hotrod.com/articles/how-gear-works/, Dec. 1, 1998, 6 pages.

NXT Health, "Patient Companion Webpage", http://nxthealth.org/patient-companion/, 2016, 4 pages.

* cited by examiner

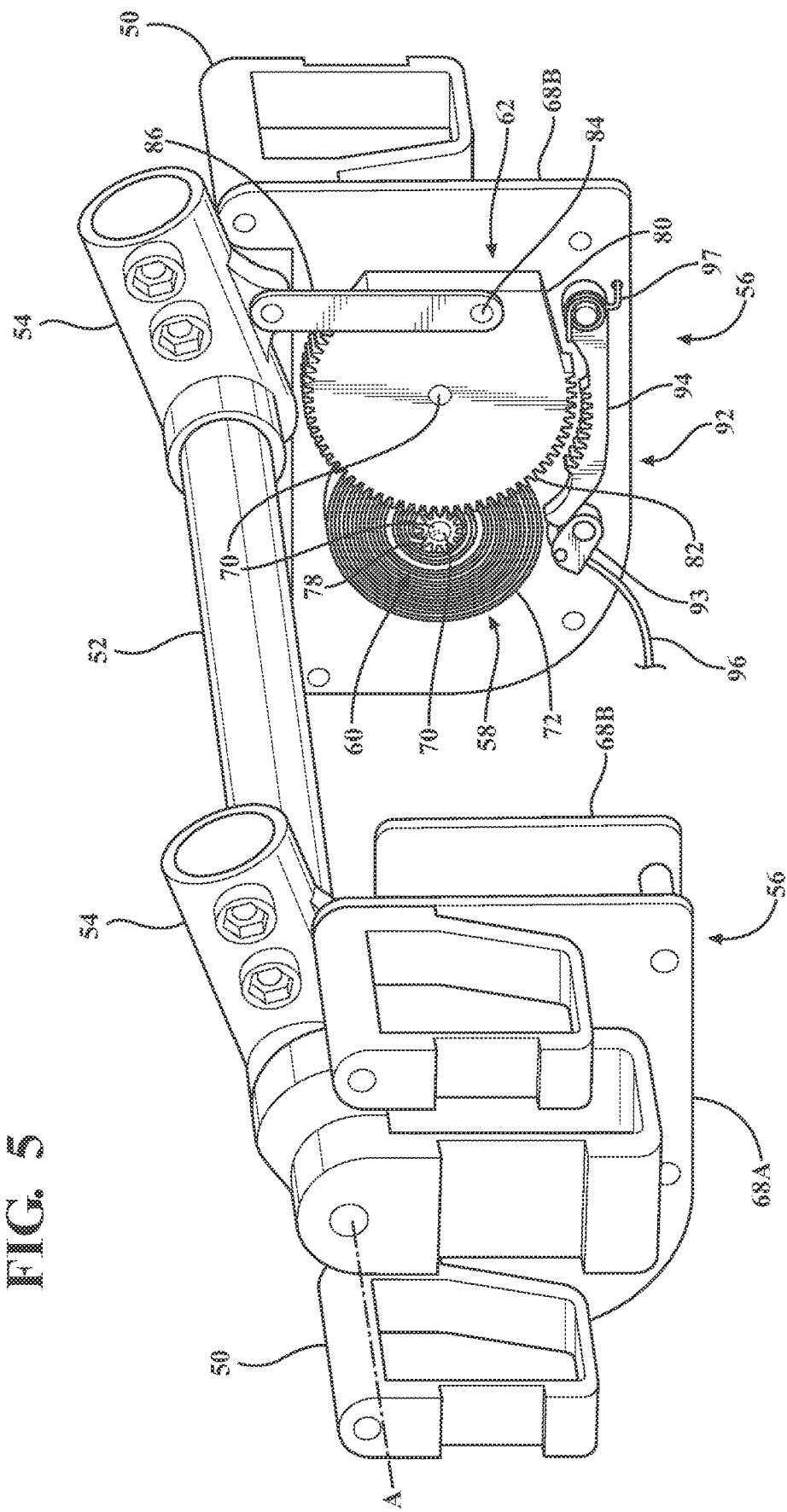

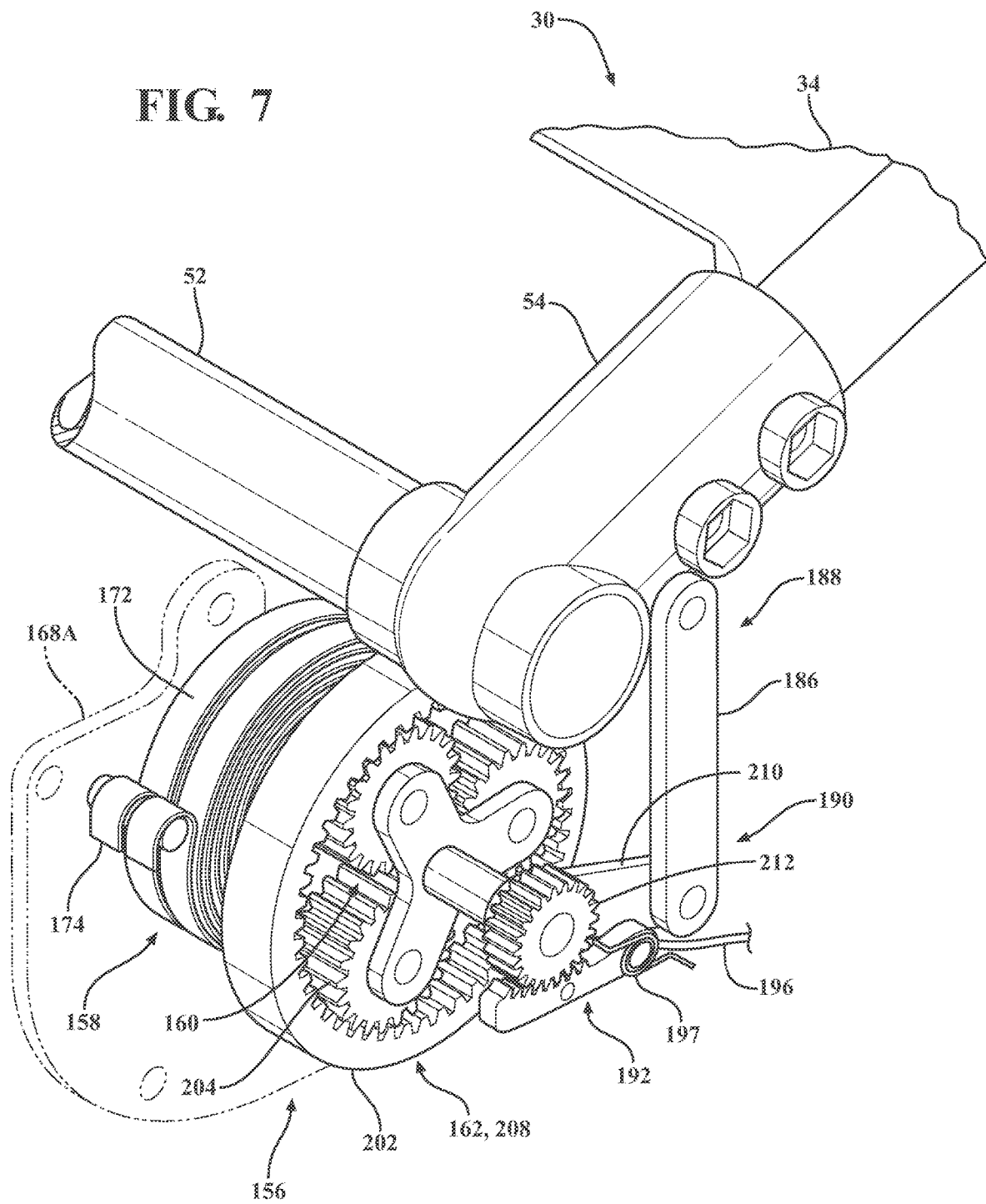

PATENT SUPPORT APPARATUS WITH DECK SECTION ACTUATOR

CROSS-REFERENCE TO RELATED APPLICATIONS

The subject patent application is a Continuation of U.S. patent application Ser. No. 16/210,886 filed on Dec. 5, 2018, which claims priority to and all the benefits of U.S. Provisional Patent Application No. 62/609,032 filed on Dec. 21, 2017, the disclosures of each of which are hereby incorporated by reference in their entirety.

BACKGROUND

Patient support apparatuses, such as hospital beds, stretchers, cots, tables, wheelchairs, and chairs are used to help caregivers facilitate care of patients in a health care setting. Patient support apparatuses generally comprise a base, a frame, and a patient support deck defining a patient support surface upon which the patient is supported. The patient support deck, in turn, generally comprises one or more movable deck sections arranged to support the patient in different positions, such as a Fowler's position. To this end, one or more of the deck sections may be designed to pivot relative to the frame.

Depending on the configuration of the patient support apparatus and the physical characteristics of the patient, it will be appreciated that it can be difficult for a caregiver to pivot the deck section into an upright position during the process of positioning the patient. Here, the patient support apparatus may be provided with an actuator, such as a gas strut, to assist with pivoting the deck section into the upright position. Occasionally, some caregivers may have difficulty overcoming biasing effects of the gas strut when attempting to pivot the deck section from an upright position into a reclined position. Furthermore, cold weather tends to cause gas struts to exert less biasing force and, in some cases, the caregiver may be required to provide additional force to pivot the deck section into the upright position.

While patient support apparatuses have generally performed well for their intended purpose, there remains a need in the art for a patient support apparatus which overcomes the disadvantages in the prior art.

BRIEF DESCRIPTION OF THE DRAWINGS

Advantages of the present invention will be readily appreciated as the same becomes better understood by reference to the following detailed description when considered in connection with the accompanying drawings.

FIG. 5 is another perspective view of the actuator of FIG. 4 shown with a housing member removed to depict a torque multiplier and a biasing device.

FIG. 7 is a partial perspective view of another embodiment of an actuator configured to facilitate movement of the deck section of the patient support deck of FIG. 4.

DETAILED DESCRIPTION

Figure 1A:
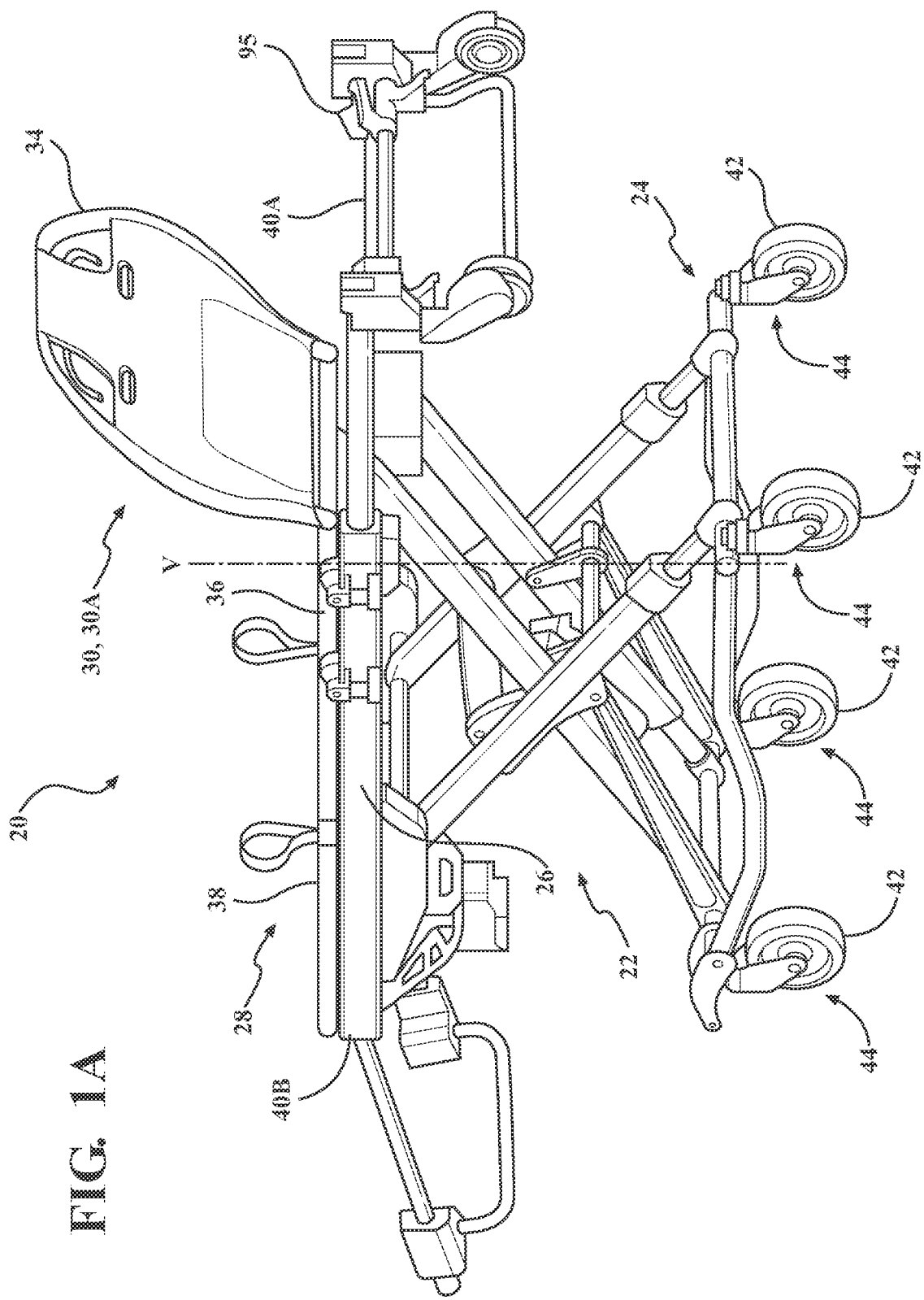
FIG. 1A is a perspective view of a patient support apparatus having a patient support deck with a deck section shown in an upright position.
Figure 1B:
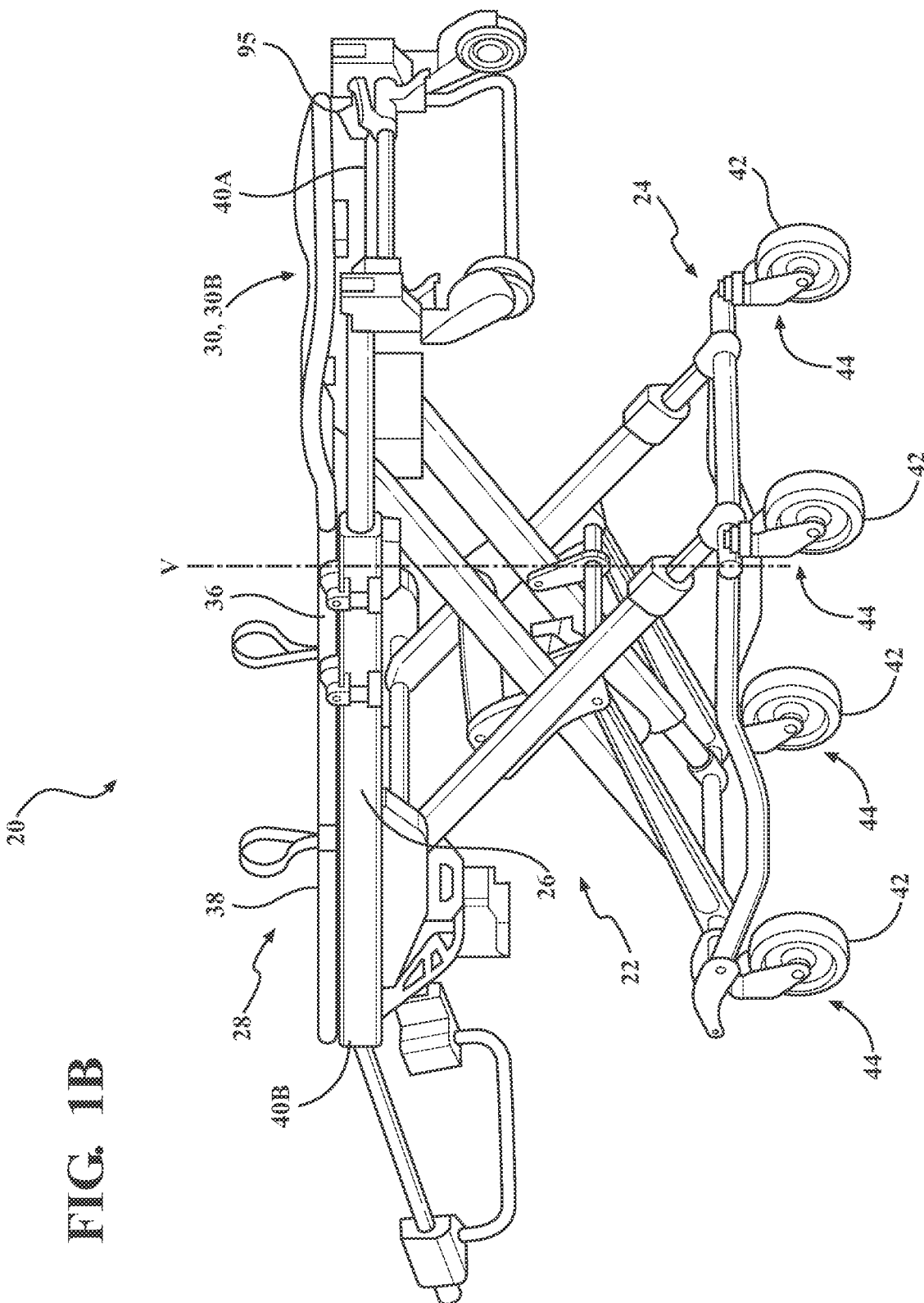
FIG. 1B is another perspective view of the patient support apparatus of FIG. 1A with the deck section shown in a lowered position.

Referring now to FIGS. 1A-1B, a patient support apparatus 20 is shown for supporting a patient. In the representative embodiment illustrated herein, the patient support apparatus 20 is realized as a mobile cot that is utilized to transport patients, such as from an emergency site to an emergency vehicle (e.g., an ambulance). However, as will be appreciated from the subsequent description below, the patient support apparatus 20 may comprise a hospital bed, a stretcher, and the like.

The patient support apparatus 20 shown in FIGS. 1A-1B comprises a support structure 22 that provides support for the patient. In the representative embodiment illustrated herein, the support structure 22 comprises a movable base 24, a support frame 26, and a patient support deck 28. The support frame 26 and the patient support deck 28 are spaced above the base 24 in FIGS. 1A-1B. As is described in greater detail below, the support frame 26 and the patient support deck 28 are arranged for movement relative to the base 24.

Figure 2:
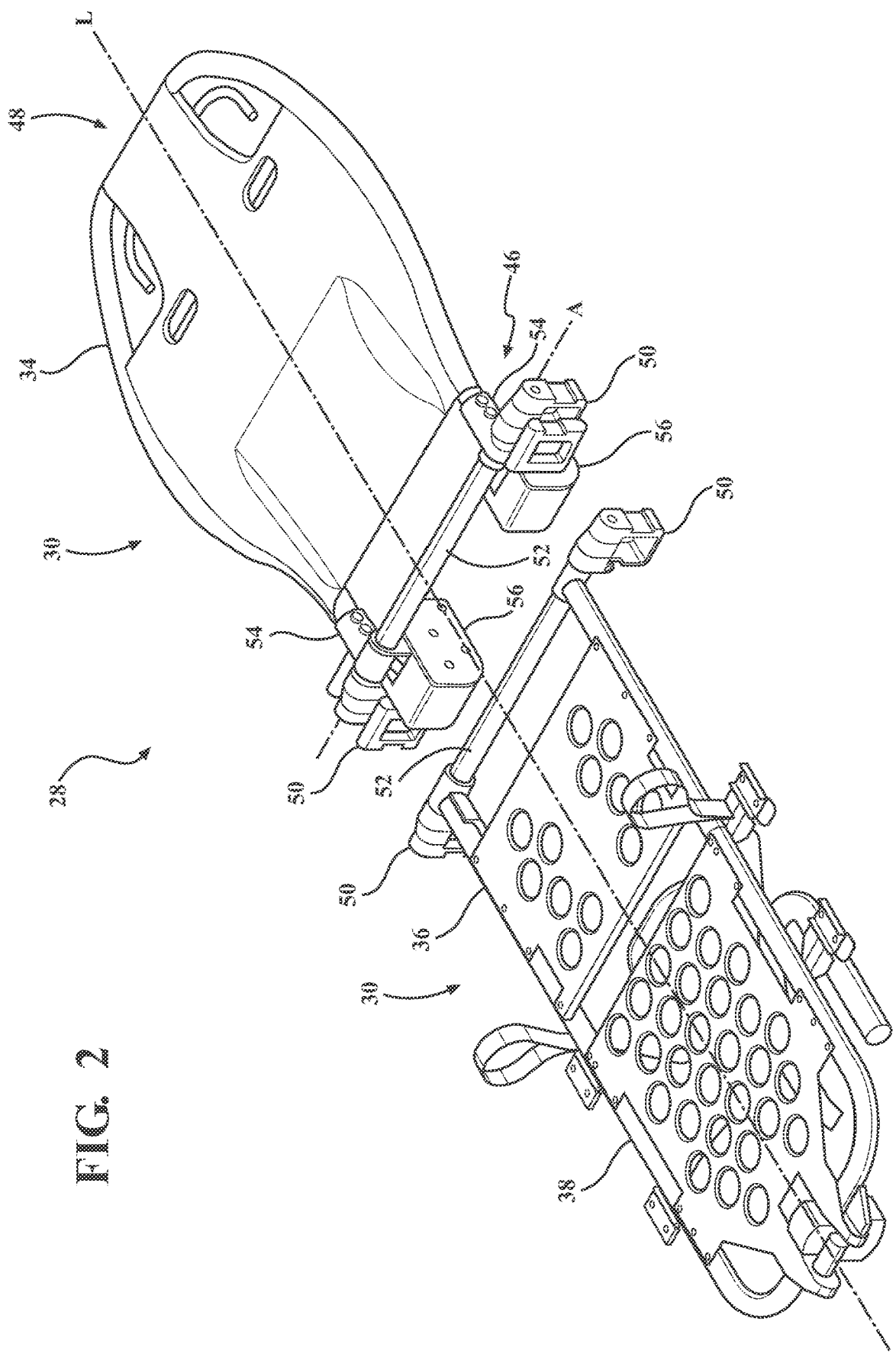
FIG. 2 is another perspective view of the patient support deck of FIGS. 1A-1B, shown with an actuator configured to facilitate movement of the deck section.

As is best depicted in FIG. 2, the patient support deck 28 has at least one deck section 30 arranged for movement relative to the support frame 26 to support the patient in different positions, orientations, and the like. The deck sections 30 of the patient support deck 28 provide a patient support surface 32 upon which the patient is supported. More specifically, in the representative embodiment of the patient support apparatus 20 illustrated herein, the patient support deck 28 has three deck sections 30 which cooperate to define the patient support surface 32: a back section 34, a seat section 36, and a leg section 38. The seat section 36 is fixed relative to the support frame 26, and the leg section 38 may be fixed or may be movable relative to the support frame 26. Other configurations are contemplated.

The base 24, the support frame 26, the patient support deck 28, and the patient support surface 32 each have a head end and a foot end corresponding to designated placement of the patient's head and feet on the patient support apparatus 20. The support frame 26 comprises a longitudinal axis L (see FIG. 2) along its length from the head end to the foot end. The support frame 26 also comprises a vertical axis V arranged crosswise (e.g., perpendicularly) to the longitudinal axis L, along which the support frame 26 may be lifted and lowered relative to the base 24. The construction of the support structure 22 may take on any known design, and is not limited to that specifically set forth herein. In addition, a mattress (not shown) may be provided in certain embodiments, such that the patient rests directly on a patient support surface of the mattress while also being supported by the patient support surface 32.

Side rails (not shown) may be coupled to the support frame 26 in some embodiments. Depending on the specific configuration of the patient support apparatus 20, it will be appreciated that there could be different types and/or arrangements of various numbers of side rails. The side rails may be fixed to the support frame 26 or may be movable between a raised position in which they block ingress and egress into and out of the patient support apparatus 20, one or more intermediate positions, and a lowered position in which they are not an obstacle to such ingress and egress. In still other configurations, such as in the illustrated embodiment, the patient support apparatus 20 may not include any side rails.

Wheels 42 are coupled to the base 24 to facilitate transport over floor surfaces. The wheels 42 are arranged in each of four quadrants of the base 24. In the embodiment shown, the wheels 42 are caster wheels able to rotate and swivel relative to the support structure 22 during transport. Each of the wheels 42 forms part of a caster assembly 44, and each caster assembly 44 is mounted to the base 24. It should be understood that various configurations of the caster assemblies 44 are contemplated. In addition, in some embodiments, the wheels 42 are not caster wheels and may be non-steerable, steerable, non-powered, powered, or combinations thereof. Additional wheels are also contemplated. For example, the patient support apparatus 20 may comprise four non-powered, non-steerable wheels, along with one or more powered wheels.

In other embodiments, one or more auxiliary wheels (powered or non-powered), which are movable between stowed positions and deployed positions, may be coupled to the support structure 22. In some cases, when these auxiliary wheels are located between caster assemblies 44 and contact the floor surface in the deployed position, they cause two of the caster assemblies 44 to be lifted off the floor surface thereby shortening a wheel base of the patient support apparatus 20. A fifth wheel may also be arranged substantially in a center of the base 24. It will be appreciated that the patient support apparatus 20 may comprise different support structure 22 configurations to support the support deck 28. For example, a stationary hospital bed may comprise a patient support deck 28 supported by a support structure 22 that rests directly on a floor surface without a discrete base 24 or wheels 42. Similarly, it is contemplated that the patient support apparatus 20 could be configured without a discrete base 24, such as with wheels 42 coupled directly to the support structure 22. Other configurations are contemplated.

In the embodiment illustrated in FIGS. 1A-2, the deck section 30 realized as the back section 34 is arranged for articulation relative to the support frame 26 between a first position 30A (see FIG. 1A) and a second position 30B (see FIG. 1B). Here, the back section 34 articulates between the first position 30A and the second position 30B about an articulation axis A (see FIG. 2). To this end, the back section 34 has a pivot end 46 proximal to the articulation axis A, and a free end 48 distal from the articulation axis A. The first position 30A, shown in FIG. 1A, is configured to support a patient in a generally upright position, such as the Fowler's position. In the first position 30A, the free end 48 is higher than the pivot end 46. Shown in FIG. 1B, the second position 30B is configured to support a patient lying flat. In the second position 30B, the free end 48 is generally at the same height as the pivot end 46. It should be appreciated that the relative heights of the pivot end 46 and the free end 48 are used herein to differentiate the first position 30A from the second position 30B with respect to the support frame 26, and may be arranged in different ways relative to the environment such as if the support deck 28 is tilted in a Trendelenburg's position (not shown). Furthermore, it will be appreciated that the first position 30A and the second position 30B can defined in a number of different ways sufficient to differentiate from each other.

In addition to the first position 30A and the second position 30B, the deck section 30 may be configured to articulate into any number of intermediate positions to support a patient more upright or less upright. For example, the back section 34 may be arranged to form a 90-degree angle with the other deck sections 36, 38 in the first position 30A, and a 0-degree angle in the second position 30B. The back section 34 may be able to be latched in intermediate positions at 15-degrees, 30-degrees, 45-degrees, 60-degrees, etc. Generally, the back section 34 pivots about the articulation axis A through an arc of at least 30-degrees between the first position 30A and the second position 30B.

Figure 3:
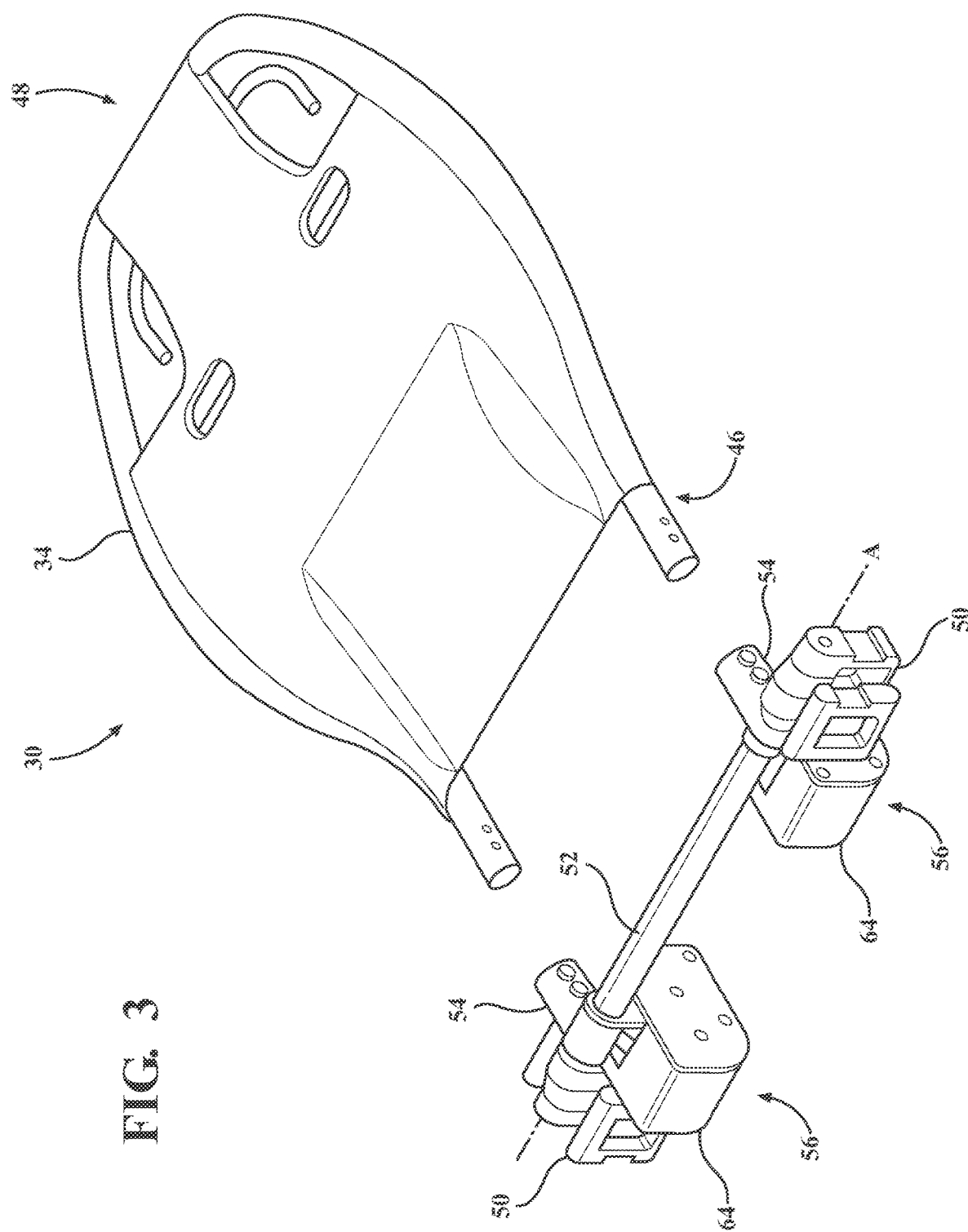
FIG. 3 is an exploded perspective view of the patient support deck and the actuator of FIG. 2.

Referring now to FIGS. 1A-3, the patient support apparatus 20 further comprises deck supports, generally indicated at 50, coupled to each of the deck sections 30 and configured to mount the respective deck sections 30 to the support frame 26. In FIGS. 2-3, the support frame 26 is omitted from view to help illustrate how the deck supports 50 are coupled to the deck sections 30. Each deck support 50 comprises a respective lateral portion 52 extending between right and left frame members 40A, 40B (or "rails") of the support frame 26. A deck coupler 54 is provided to facilitate articulation of the back section 34 relative to the support frame 26. The deck coupler 54 is disposed at the pivot end 46 of the back section 34 and couples the back section 34 to the support frame 26. In the embodiment shown, the deck coupler 54 is coupled to the deck support 50 and supports the deck section 30 for rotation about the articulation axis A.

The patient support apparatus 20 further comprises an actuator 56 interposed in force-translating relation between the support frame 26 and the back section 34. The actuator 56 is coupled to the support frame 26 and is configured to store energy in response to articulation of the back section 34 from the first position 30A toward the second position 30B. The stored mechanical energy may then be released to urge the back section 34 back toward the first position 30A. In the embodiment shown, the patient support apparatus 20 is equipped with two actuators 56: one actuator 56 coupled to each of the right and left sides of the support frame 26, respectively corresponding to the right frame member 40A and the left frame member 40B. However, it is contemplated that the patient support apparatus 20 may have only a single actuator 56, such as centered between the left and right sides or offset toward one of the sides. Furthermore, it will be appreciated that more than two actuators 56 may be utilized in some embodiments, depending on the specific configuration of the patient support apparatus. Moreover, where more than one of the deck sections 30 is movable, the patient support apparatus 20 may comprise one or more actuators 56 for each movable deck section 30. Other configurations are contemplated.

Referring now to FIGS. 4-6B, a first embodiment of the actuator 56 is shown. The actuator 56 comprises a biasing device 58 (see FIG. 5) having an interface 60, and a torque multiplier 62 coupled to the back section 34. As is described in greater detail below, the biasing device 58 is configured to store mechanical energy via the interface 60, and the torque multiplier 62 is engaged with the interface 60 to translate mechanical energy stored in the biasing device 58 into force acting on the back section 34 to urge the back section 34 toward the first position 30A. When the back section 34 is articulated from the first position 30A toward the second position 30B, mechanical energy is translated through the torque multiplier 62 and is stored in the biasing device 58. Conversely, mechanical energy stored in the biasing device 58 is translated through the torque multiplier 62 into force acting toward the back section 34 to urge the back section 34 toward the first position 30A from the second position 30B.

The actuator 56 further comprises a cover 64 defining an interior. The cover 64 is arranged such that the biasing device 58 and the torque multiplier 62 are disposed within the interior. The cover 64 helps prevent ingress of foreign objects, the presence of which may otherwise impair operation by becoming stuck in the actuator 56. The cover 64 also helps prevent a patient or caregiver from accessing the interior during use of the patient support apparatus 20.

Figure 4:
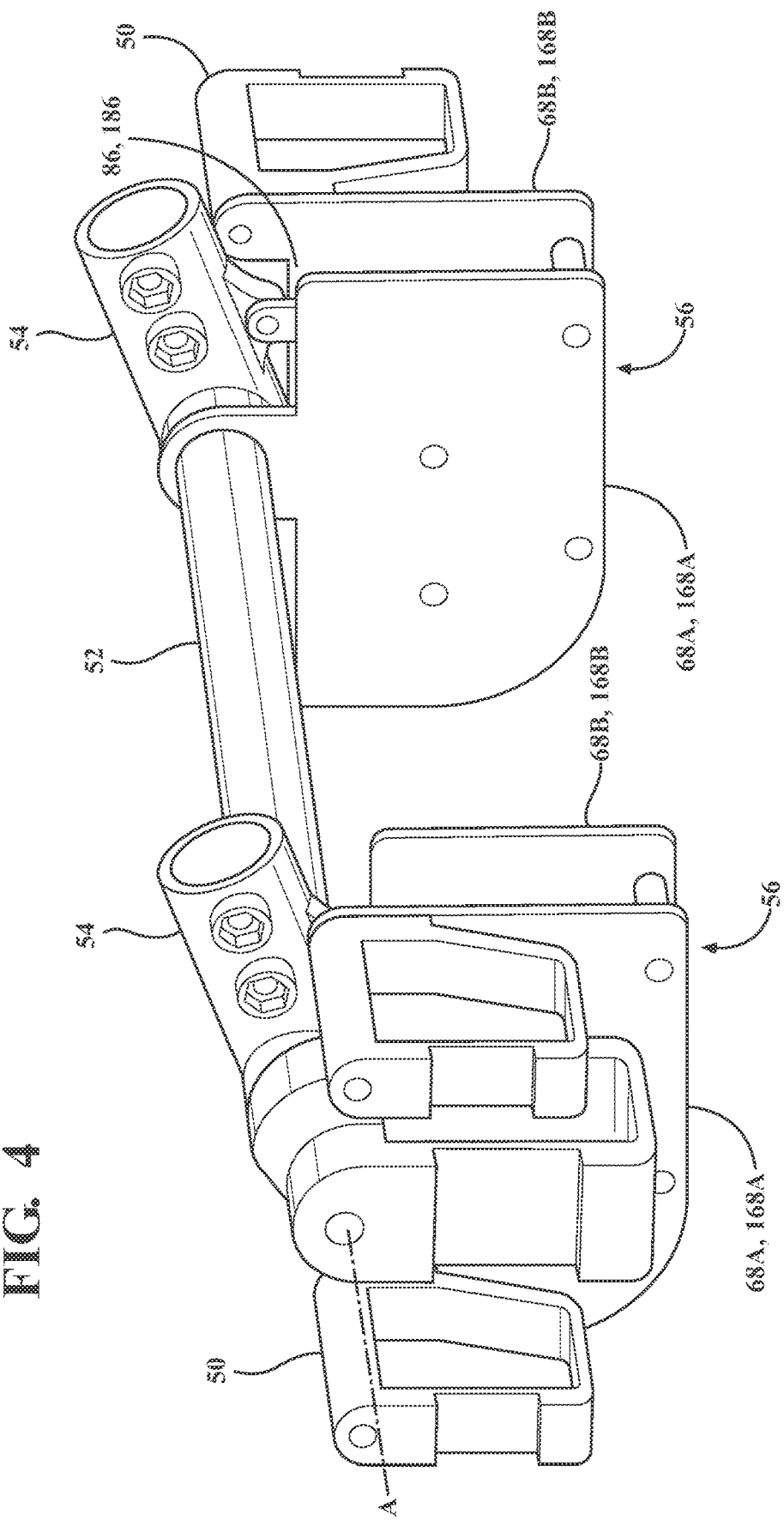
FIG. 4 is a perspective view of one embodiment of the actuator of FIGS. 2-3 shown with a cover removed.
Figure 6A:
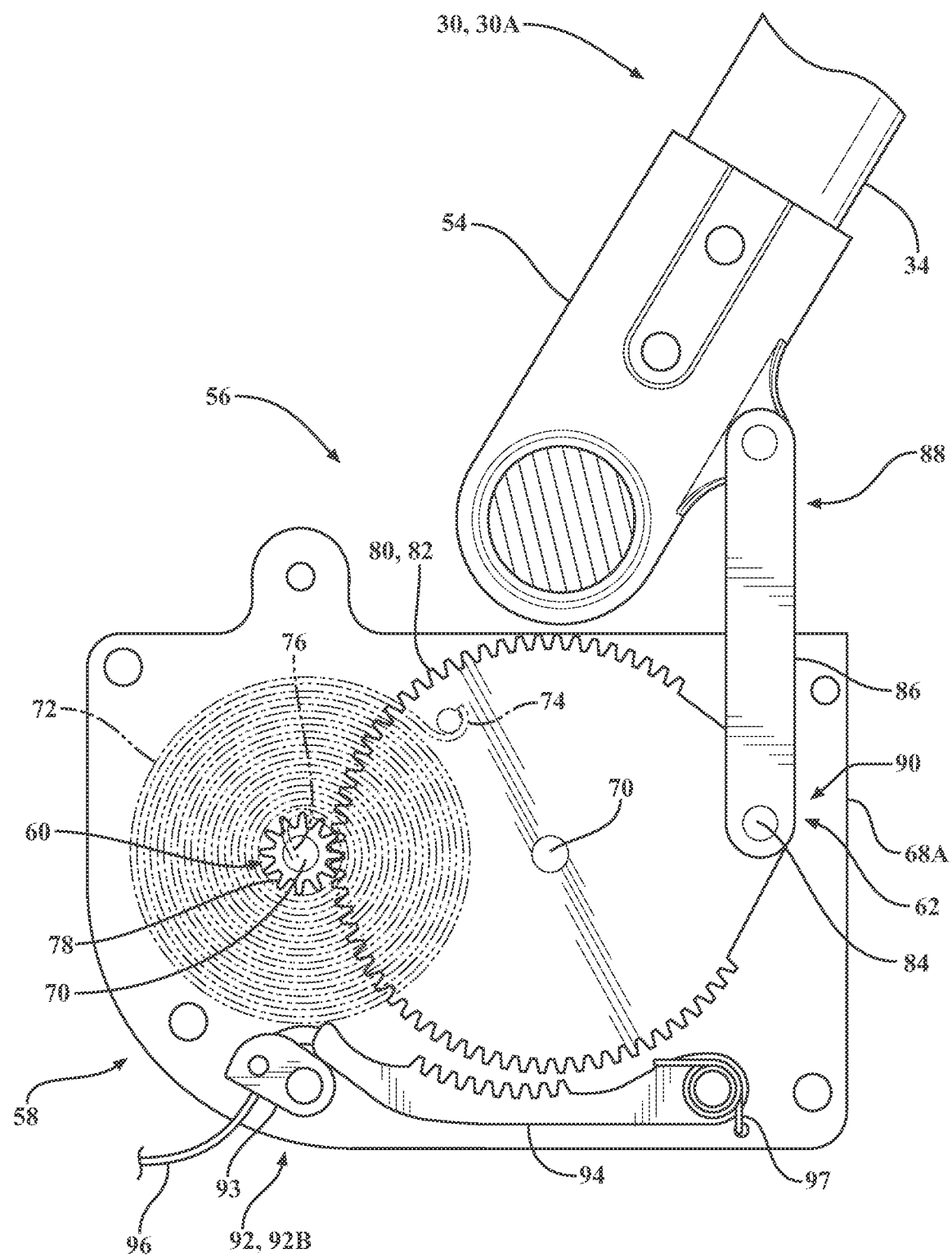
FIG. 6A is a side view of the actuator of FIG. 5 shown having a latch mechanism arranged in a disengaged position.
Figure 6B:
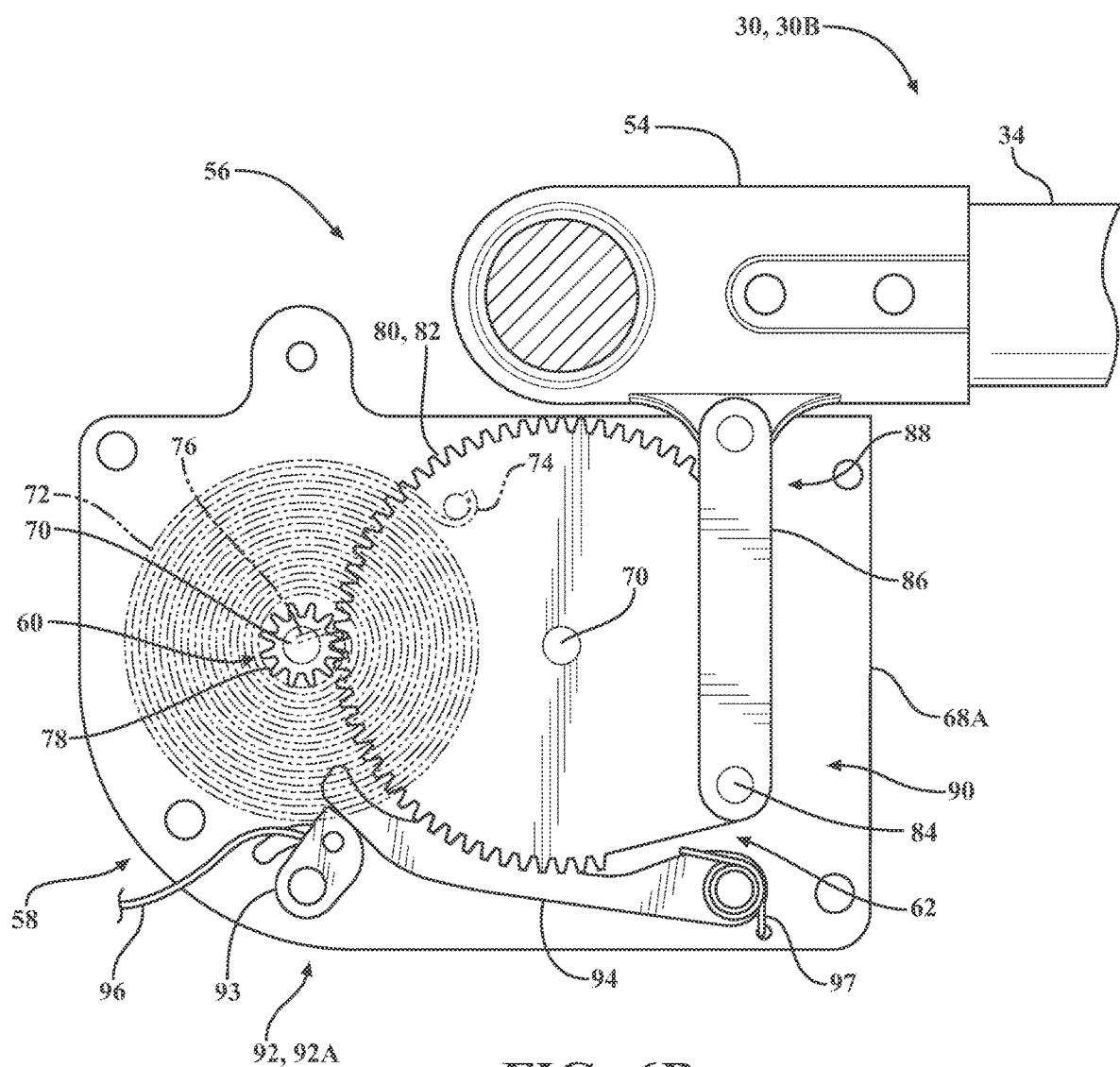
FIG. 6B is another side view of the actuator of FIG. 6A shown with the latch mechanism arranged in an engaged position.

Referring specifically to FIGS. 4 and 5, the actuator 56 comprises first and second housing members 68A, 68B. The housing members 68A, 68B are coupled to the support frame 26 and support the various components of the actuator 56. The housing members 68A, 68B are spaced from each other, with the biasing device 58 and the torque multiplier 62 disposed therebetween. Shafts 70 extend between each of the housing members 68A, 68B to rotatably support the torque multiplier 62 and the biasing device 58.

The biasing device 58 comprises a resiliently flexible biasing element 72 coupled to the interface 60. In the representative embodiment illustrated in FIGS. 6A-6B, the biasing element 72 is realized as a spiral torsion spring. However, as will be appreciated from the subsequent description below, the biasing element 72 could be configured in a number of different ways sufficient to resiliently deform to store mechanical energy as the deck section 30 moves from the first position 30A to the second position 30B. The biasing element 72 has a first spring end 74 fixedly coupled to one of the housing members 68A, and a second spring end 76 movable relative to the first spring end 74. In the illustrated embodiment, the biasing element 72 stores mechanical energy by winding the second spring end 76 about one of the shafts 70. Here, the second spring end 76 is coupled to the interface 60 of the biasing device 58 such that the interface 60 winds the second spring end 76. The interface 60 of the biasing device 58 may comprise a pinion gear 78 engaged with the second spring end 76. The pinion gear 78 is rotatably supported on the shaft 70 such that rotation of the pinion gear 78 winds or unwinds the second spring end 76.

The torque multiplier 62 may comprise a drive gear 80 having a toothed portion with gear teeth 82 and a pin boss 84. The drive gear 80 is rotatably supported on one of the shafts 70 and is disposed in meshed engagement with the pinion gear 78. Put differently, the drive gear 80 engages the pinion gear 78 in rotational communication such that rotation of the drive gear 80 facilitates rotation of the interface 60, and vice versa. It should be appreciated that the torque multiplier 62 may transfer mechanical energy to the biasing device 58 in different ways, such as without the use of a drive gear 80 or a pinion gear 78. For example, the torque multiplier may comprise a belt and pulley arrangement. Other configurations are contemplated.

Generally, the pinion gear 78 rotates at a rate greater than the drive gear 80. Each of the pinion gear 78 and the drive gear 80 have a respective size defined by a diameter measurement, or a number of teeth. The drive gear 80 has a drive gear size and the pinion gear 78 has a pinion gear size. The drive gear 80 and the pinion gear 78 rotate at a ratio of the drive gear size to the pinion gear size. The ratio of the drive gear size to the pinion gear size may be 6:1. The ratio is generally greater than 1:1 such that the pinion gear 78 rotates faster than the drive gear 80. Other ratios are possible, such as 1:1, 2:1, 3:1, etc.

The torque multiplier 62 further comprises a link 86 to transmit force between the drive gear 80 and the back section 34. The link 86 has a first link end 88 rotatably coupled to the back section 34 (e.g. via a pivot pin), and a second link end 90 rotatably coupled to the pin boss 84. The first link end 88 is spaced from the second link end 90. Movement of the back section 34 transfers force to the drive gear 80 via the link 86, thereby causing the drive gear 80 to rotate. Likewise, rotation of the drive gear 80 transfers force to the link 86 to move the back section 34.

The patient support apparatus 20 further comprises a latch mechanism 92 coupled to the actuator 56. The latch mechanism 92 is arranged for selective engagement with the torque multiplier 62 and is movable between an engaged position 92A (see FIG. 6B), and a disengaged position 92B (see FIG. 6A). In the engaged position 92A, the latch mechanism 92 restricts articulation of the back section 34. Conversely, in the disengaged position 92B, the latch mechanism 92 allows the back section 34 to articulate. To this end, the latch mechanism 92 comprises a cam 93 and a pawl 94. The pawl 94 is pivotably coupled to the housing member 68A (e.g. via a pivot pin) and has pawl teeth selectively engageable with the gear teeth 82 of the drive gear 80. In the engaged position 92A, the cam 93 forces the pawl 94 into engagement with the gear teeth 82 to prevent rotation of the drive gear 80. In the disengaged position 92B, the cam 93 allows the pawl 94 to move away from and out of engagement with the gear teeth 82, thereby allowing the drive gear 80 to rotate.

The caregiver can move the latch mechanism 92 between the engaged position 92A and the disengaged position 92B via a lever 95 (see FIGS. 1A and 1B) that is operatively coupled to the cam 93. The lever 95 may be located either remotely from the cam 93, or may be directly coupled to the cam 93. In one embodiment, the lever 95 is mounted to the support frame 26. A cable 96 may be coupled to the lever 95 and to the cam 93 such that movement of the lever 95 applies tension to the cable 96 used to actuate the cam 93. Alternatively, the cam 93 may be actuated by a linkage, an electrical motor, a solenoid, and other types of actuators known in the art. The latch mechanism 92 further comprises a cam biasing device, such as a spring 97 that biases the cam 93 toward the engaged position 92A. Other configurations are contemplated.

When the back section 34 is in the first position 30A, the caregiver may wish to lower the back section 34 into the second position 30B. To this end, the caregiver can move the latching mechanism 92 into the disengaged position 92B by engaging the lever 95. Here, the lever 95 tensions the cable 96 which, in turn, moves the cam 93 and disengages the pawl 94 from the drive gear 80. When the latch mechanism 92 is in the disengaged position 92B, the back section 34 can be moved toward the second position 30B. To this end, the caregiver can apply force to the free end 48 of the back section 34 so as to articulate the back section 34 about the articulation axis A, which transfers force to the torque multiplier 62. The torque multiplier 62, in turn, translates the force acting on the back section 34 into rotation of the drive gear 80 via the link 86. Here, rotation of the drive gear 80 is transferred to the biasing device 58 via the interface 60; the drive gear 80 rotates the pinion gear 78 which, in turn, winds the second end 76 of the biasing element 72 to store mechanical energy in the biasing device 58. When the back section 34 reaches the desired second position 30B, the caregiver can then move the latching mechanism 92 to the engaged position 92B to prevent subsequent inadvertent movement of the back section 34 away from the second position 30B.

When the back section 34 is in the second position 30B, the caregiver may wish to raise the back section 34 into the first position 30A. To this end, the caregiver can move latching mechanism 92 into the disengaged position 92B by engaging the lever 95. Here, the lever 95 tensions the cable 96 which, in turn, moves the cam 93 and disengages the pawl 94 from the drive gear 80. With the latch mechanism 92 is in the disengaged position 92B, mechanical energy stored in the biasing device 58 is released and translates through the torque multiplier 62 to move the back section 34 toward the first position 30A. To this end, the second end 76 of the biasing element 72 rotates the pinion gear 78 to rotate the drive gear 80. The drive gear 80 rotates more slowly than the pinion gear 78, as noted above, which slows or otherwise limits the rate at which the back section 34 articulates toward the first position 30A as the torque multiplier 62 translates the mechanical energy stored in the biasing device 58 into force acting on the back section 34 to urge the free end 48 upward. When the back section 34 reaches the desired first position 30A, the caregiver can then move the latching mechanism 92 to the engaged position 92B to prevent subsequent inadvertent movement of the back section 34 away from the first position 30A. It should be appreciated that the preceding description of the operation of the actuator 56 is not limited to operation between the first position 30A and the second position 30B, but any of the intermediate positions depending on the direction that the caregiver desires to move the back section 34.

Turning now to FIGS. 4 and 7-8B, a second embodiment of the actuator 156 is shown. This embodiment is similar to the embodiment of the actuator 56 described above, and likewise comprises a biasing device 158 having an interface 160, and a torque multiplier 162 coupled to the back section 34. The biasing device 158 is similarly configured to store mechanical energy via the interface 160, and the torque multiplier 162 is engaged with the interface 160 to translate mechanical energy stored in the biasing device 158 into force acting on the back section 34 to urge the back section 34 toward the first position 30A. Here too, when the back section 34 is articulated toward the second position 30B, mechanical energy is translated through the torque multiplier 162 and is stored in the biasing device 158, and mechanical energy stored in the biasing device 158 is likewise translated through the torque multiplier 162 into force acting toward the back section 34 to urge the back section 34 toward the first position 30A.

Figure 8A:
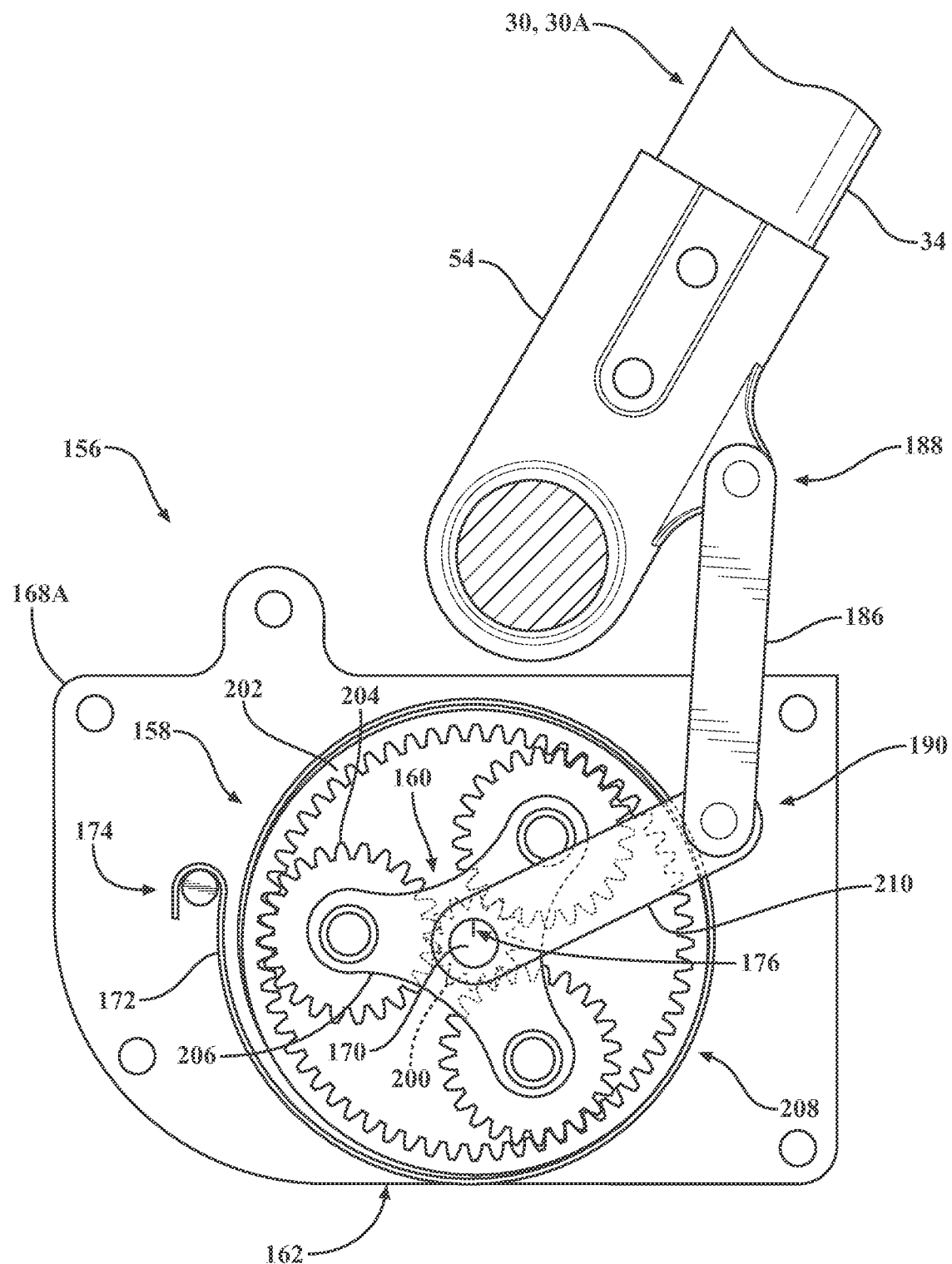
FIG. 8A is a side view of the actuator of FIG. 7 shown arranged in a first position.
Figure 8B:
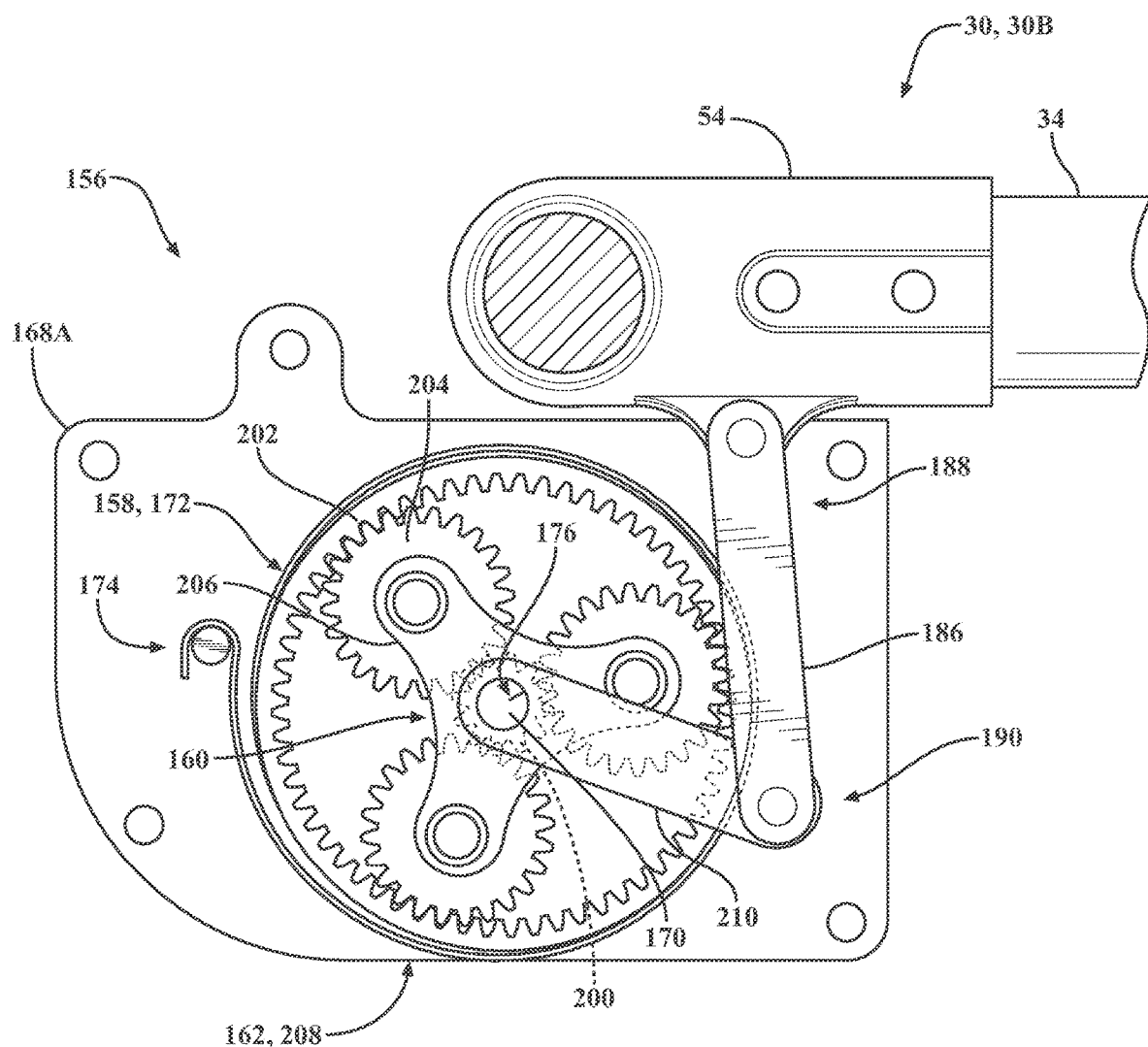
FIG. 8B is another side view of the actuator of FIG. 8A shown arranged in a second position.

In this embodiment, the actuator 156 likewise comprises first and second housing members 168A, 168B. The housing members 168A, 168B are coupled to the support frame 26 to support the actuator 156. The housing members 168A, 168B are spaced from each other with the biasing device 158 and the torque multiplier 162 disposed therebetween. Here too, a shaft 170 extends between each of the housing members 168A, 168B to rotatably support the torque multiplier 162 and the biasing device 158. Likewise, the biasing device 158 further comprises at least one resiliently flexible biasing element 172 coupled to the interface 160. The biasing element 172 may be a spiral torsion spring, such as shown in FIGS. 8A and 8B. The biasing element 172 has a first spring end 174 fixedly coupled to one of the housing members 168A, and a second spring end 176 movable relative to the first spring end 174. The biasing element 172 stores mechanical energy by winding the second spring end 176 on the shaft 170. The second spring end 176 is coupled to the interface 160 of the biasing device 158 such that the interface 160 winds the second spring end 176.

In the second embodiment of the actuator 156, the interface 160 of the biasing device 158 comprises a sun gear 200, and the torque multiplier 162 comprises a ring gear 202, planet gears 204, and a planet carrier 206. The sun gear 200 rotates about the same shaft 170 as the second spring end 176 to wind the second spring end 176. The planet gears 204 are arranged between and are engaged with the ring gear 202 and the sun gear 200 such that the sun gear 200, the planet gears 204, and the ring gear 202 define a planetary gearset 208. The planetary gearset 208 translates mechanical energy stored in the biasing device 158 into force acting on the back section 34 to urge the back section 34 toward the first position 30A. The planetary gearset 208 has a planetary reduction ratio of 6:1 such that the sun gear 200 rotates faster than the planet carrier 206. However, other ratios are contemplated, such as 1:1, 2:1, 3:1, etc.

The planet carrier 206 comprises a radially extending arm portion 210 that serves as a crank. The torque multiplier 162 further comprises a link 186 to transmit force between the biasing device 158 and the back section 34. The link 186 has a first link end 188 spaced from a second link end 190. The first link end 188 is rotatably coupled to the back section 34, and the second link end 190 is rotatably coupled to the arm portion 210 of the planet carrier 206 (see FIG. 7). Movement of the back section 34 transfers force via the link 186 to the arm portion 210, which causes the planet carrier 206 to rotate. Likewise, rotation of the planet carrier 206 moves the arm portion 210 and transfers force to the link 186 to move the back section 34.

Similar to the first embodiment of the actuator 56 described above, the patient support apparatus 20 may comprises a latch mechanism 192 coupled to the second embodiment of the actuator 156. In this embodiment, the latch mechanism 192 is similarly arranged for selective engagement with the torque multiplier 162 and is movable between an engaged position and a disengaged position (not shown in detail). In the engaged position, the latch mechanism 192 restricts articulation of the back section 34. Conversely, in the disengaged position, the latch mechanism 192 allows the back section 34 to articulate. To this end, the latch mechanism 192 comprises a pawl 194, and a detent wheel 212 coupled to the arm portion 210. The pawl 194 is pivotably coupled to the housing member 168A (e.g. via a pivot pin) and has pawl teeth selectively engageable with the detent wheel 212. In the engaged position, the pawl teeth mesh with the detent wheel 212 to prevent rotation of the planet carrier 206. In the disengaged position, the pawl 194 is spaced from and is out of engagement with the detent wheel 212, thereby allowing the planet carrier 206 to rotate.

The caregiver can move the latch mechanism 192 between the engaged position and the disengaged position by engaging the lever 95 (see FIGS. 1A and 1B) which, in this embodiment, is likewise operatively coupled to the pawl 194. The lever 95 may be located either remotely from the cam 93, or directly coupled to the pawl 194. In one embodiment, the lever 95 is mounted to the support frame 26. A cable 196 may be coupled to the lever 95 and to the pawl 194 such that movement of the lever 95 applies tension to the cable 196 to actuate the pawl 194. Alternatively, the pawl 194 may be actuated by a linkage, an electrical motor, a solenoid, and other actuators known in the art. The latch mechanism 192 further comprises a pawl biasing device, such as a spring 197 that biases the pawl 194 toward the engaged position. Other configurations are contemplated.

When the back section 34 is in the first position 30A, the caregiver may wish to lower the back section 34 into the second position 30B. To this end, the caregiver can move the latching mechanism 192 into the disengaged position by engaging the lever 95. Here, the lever 95 tensions the cable 196 which, in turn, causes the pawl 194 to disengage from the detent wheel 212. When the latch mechanism 192 is disengaged, the back section 34 can be moved toward the second position 30B. To this end, the caregiver can apply force to the free end 48 of the back section 34 to articulate the back section 34 about the articulation axis A, which transfers force to the torque multiplier 162. The torque multiplier 162, in turn, translates the force acting on the back section 34 into rotation of the planet carrier 206 via the link 186. Here, rotation of the planet carrier 206 is transferred to the biasing device 158 via the interface 160; the planet carrier 206 rotates the planet gears 204 which, in turn, rotate the sun gear 200 to wind the second end 176 of the biasing element 172 to store mechanical energy in the biasing device 158. When the back section 34 reaches the desired second position 30B, the caregiver can then move the latching mechanism 192 to the engaged position to prevent subsequent inadvertent movement of the back section 34 away from the second position 30B.

When the back section 34 is in the second position 30B, the caregiver may wish to raise the back section 34 into the first position 30A. To this end, the caregiver can move the latching mechanism 192 into the disengaged position by engaging the lever 95. Here, the lever 95 tensions the cable 196 which, in turn, disengages the pawl 194 from the detent wheel 212. When the latch mechanism 192 is disengaged, mechanical energy stored in the biasing device 158 is released and translates through the torque multiplier 162 to move the back section 34 toward the first position 30A. To this end, the second end 176 of the biasing element 172 rotates the sun gear 200 to rotate the planet gears 204 and the planet carrier 206. The planet carrier 206 rotates more slowly than the sun gear 200, which slows or otherwise limits the rate at which the back section 34 articulates toward the first position 30A as the torque multiplier 162 translates the mechanical energy stored in the biasing device 158 into force acting on the back section 34 to urge the free end 48 upward. When the back section 34 reaches the desired first position 30A, the caregiver can move the latching mechanism 192 to the engaged position to prevent subsequent inadvertent movement of the back section 34 away from the first position 30A. Here too, it should be appreciated that the preceding description of the operation of the actuator 156 is not limited to operation between the first position 30A and the second position 30B, but any of the intermediate positions depending on the direction that the caregiver desires to move the back section 34.

Figure 9:
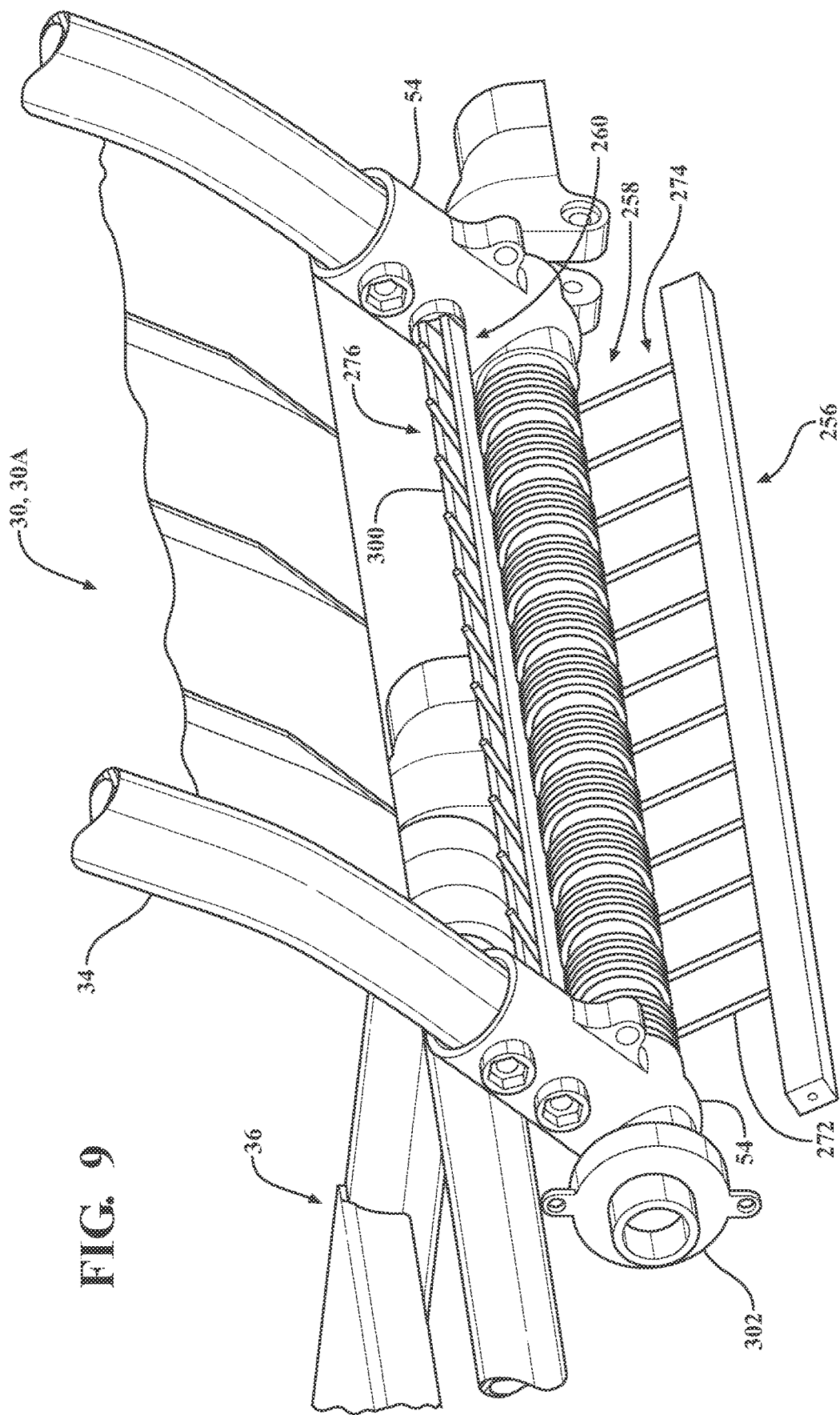
FIG. 9 is a partial perspective view of another embodiment of an actuator configured to facilitate movement of the deck section of the patient support deck of FIGS. 1A-1B.

Turning now to FIG. 9, a third embodiment of the actuator 256 is shown. Similar to the first and second embodiments of the actuator 56, 156 described above, the third embodiment of the actuator 256 also comprises a biasing device 258 having an interface 260. The biasing device 258 is likewise configured to store and translate mechanical energy into force acting on the back section 34 to urge the back section 34 toward the first position 30A. Here too, when the back section 34 is articulated toward the second position 30B, mechanical energy is translated and stored in the biasing device 258. Conversely, mechanical energy stored in the biasing device 258 as the back section 34 is moved to the second position 30B is translated into force acting on the back section 34 to urge the back section 34 back toward the first position 30A.

The biasing device 258 further comprises a resiliently flexible biasing element 272 coupled to the interface 260. The biasing element 272 may be a torsion spring that has a first spring end 274 coupled to the support frame 26, and a second spring end 276 coupled to the interface 260 and movable relative to the first spring end 274. In this embodiment, the interface 260 comprises a spring retainer 300 coupled to the back section 34, and is movable with the back section 34 to move the second spring end 276 relative to the first spring end 274.

The actuator 256 may further comprise a damper 302 coupled to the biasing device 258 which is configured to retard translation of mechanical energy stored in the biasing device 258 to the back section 34, such as when the back section 34 articulates from the first position 30A to the second position 30B. The damper 302 is coupled between the deck coupler 54 and the support frame 26, and prevents the back section 34 from articulating between the second position 30B and the first position 30A too rapidly. The damper 302 exerts increasing damping force as the back section 34 articulates at increasing rates, thereby retarding the translation of mechanical energy. A detent mechanism (not shown) may be provided to latch the back section 34 in the second position 30B. The detent mechanism may further be configured to latch the back section 34 in intermediate positions between the first position 30A and the second position 30B.

Figure 10:
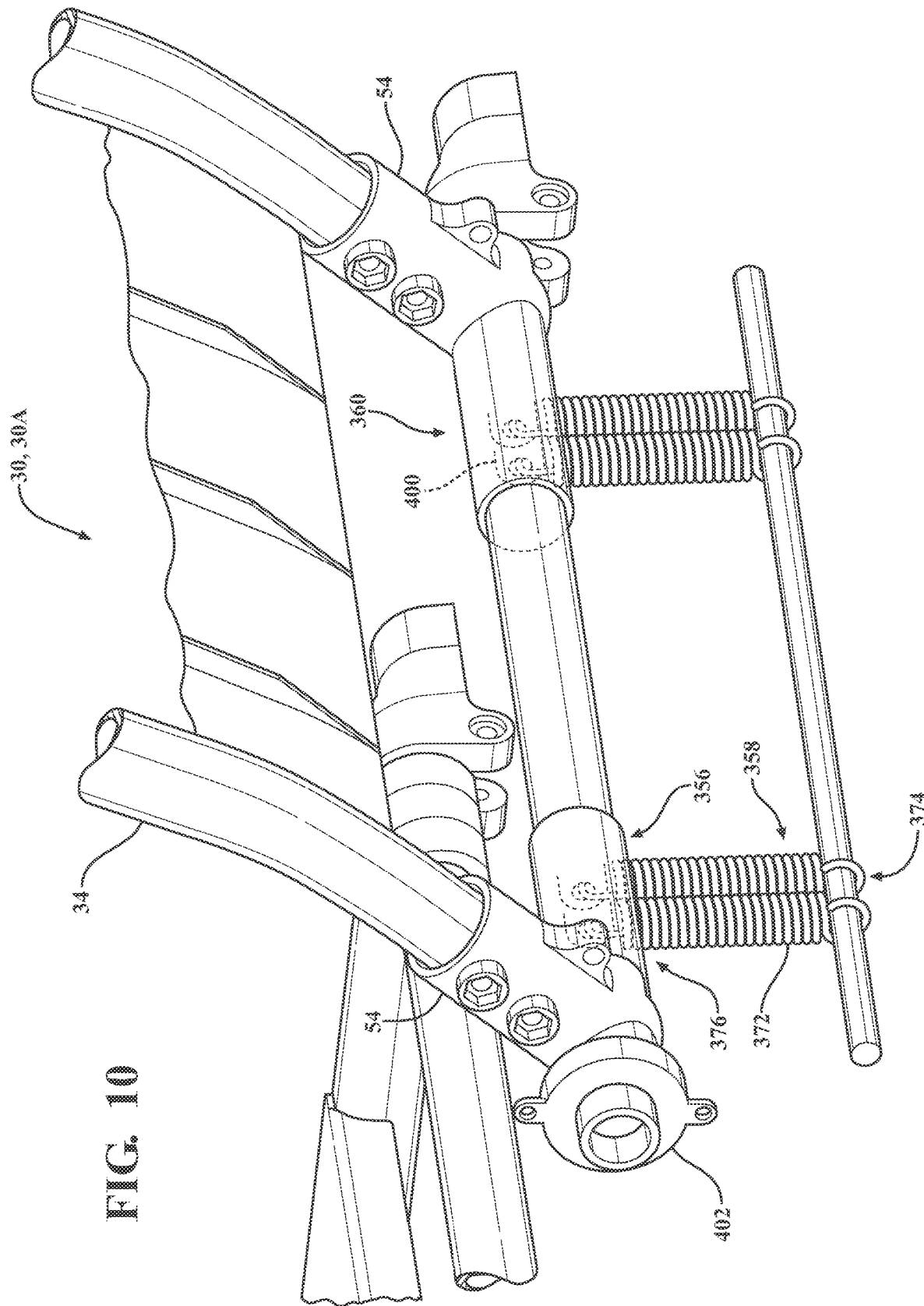
FIG. 10 is a partial perspective view of another embodiment of an actuator configured to facilitate movement of the deck section of the patient support deck of FIGS. 1A-1B.

Turning now to FIG. 10, a fourth embodiment of the actuator 356 is shown. Similar to the previous embodiments of the actuator 56, 156, 256 described above, the fourth embodiment of the actuator 356 also comprises a biasing device 358 having an interface 360. The biasing device 358 is likewise configured to store and translate mechanical energy into force acting on the back section 34 to urge the back section 34 toward the first position 30A. Here too, when the back section 34 is articulated toward the second position 30B, mechanical energy is translated and stored in the biasing device 358. Conversely, mechanical energy stored in the biasing device 358 when the back section 34 is moved to the second position 30B is translated into force acting on the back section 34 to urge the back section 34 toward the first position 30A.

The biasing device 358 further comprises a resiliently flexible biasing element 372 coupled to the interface 360. The biasing element 372 may be an extension spring that has a first spring end 374 coupled to the support frame 26, and a second spring end 376 coupled to the interface 360 and movable relative to the first spring end 374. In this embodiment, the interface 360 comprises a spring retainer 400 coupled to the back section 34, and is movable with the back section 34 to move the second spring end 376 relative to the first spring end 374.

The actuator 356 may further comprise a damper 402 coupled to the biasing device 358 which is configured to retard translation of mechanical energy stored in the biasing device 358 to the back section 34, such as when the back section 34 articulates between the first position 30A and the second position 30B. The damper 402 is coupled between the deck coupler 54 and the support frame 26, and prevents the back section 34 from articulating from the second position 30B to the first position 30A too rapidly. Here too, the damper 402 exerts increasing damping force as the back section 34 articulates at increasing rates, thereby retarding the translation of mechanical energy. A detent mechanism (not shown) may be provided to latch the back section 34 in the second position 30B. The detent mechanism may be further be configured to latch the back section 34 in intermediate positions between the first position 30A and the second position 30B.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

What is claimed is:

1. A patient support apparatus for supporting a patient, the patient support apparatus comprising:
    a support frame;
    a support deck coupled to the support frame and having a deck section arranged to articulate relative to the support frame between a first position and a second position with the deck section being arranged closer to the support frame in the second position than in the first position; and
    an actuator interposed in force-translating relation between the support frame and the deck section, the actuator comprising:
        a biasing device configured to store mechanical energy and having an interface, and
        a torque multiplier coupled to the deck section and engaged with the interface to translate potential energy stored in the biasing device into kinetic energy via an articulation force to effect active movement of the deck section urging the deck section from the second position toward the first position.

2. The patient support apparatus according to claim 1, wherein the actuator is configured such that mechanical energy is stored in the biasing device in response to articulation of the deck section toward the second position, and such that mechanical energy stored in the biasing device is translated into force acting toward the deck section to urge the deck section toward the first position.

3. The patient support apparatus according to claim 2, wherein the interface comprises a pinion gear; and
    wherein the torque multiplier comprises a drive gear disposed in rotational communication with the pinion gear.

4. The patient support apparatus according to claim 3, wherein the drive gear has a drive gear size, the pinion gear has a pinion gear size, and a ratio of the drive gear size to the pinion gear size is greater than 1:1.

5. The patient support apparatus according to claim 3, wherein the torque multiplier further comprises a link to transmit force between the drive gear and the deck section, the link having a first link end and a second link end with the first link end rotatably coupled to the deck section and with the second link end rotatably coupled to the drive gear.

6. The patient support apparatus according to claim 3, further comprising a latch mechanism coupled to the actuator and arranged for selective engagement with the torque multiplier to restrict articulation of the deck section.

7. The patient support apparatus according to claim 6, wherein the drive gear comprises gear teeth, and
    wherein the latch mechanism comprises a pawl selectively engageable with the gear teeth of the drive gear to prevent rotation of the drive gear.

8. The patient support apparatus according to claim 2, wherein the interface comprises a sun gear; and
    wherein the torque multiplier comprises a ring gear and planet gears, wherein the planet gears are arranged between and engaged with the ring gear and the sun gear such that the sun gear, the planet gears, and the ring gear define a planetary gearset to translate mechanical energy stored in the biasing device into force acting on the deck section to urge the deck section toward the first position.

9. The patient support apparatus according to claim 8, wherein the torque multiplier further comprises a link to transmit force between the planetary gearset and the deck section, the link having a first link end and a second link end with the first link end rotatably coupled to the deck section and with the second link end rotatably coupled to the planetary gearset.

10. The patient support apparatus according to claim 8, further comprising a latch mechanism coupled to the actuator and arranged for selective engagement with the torque multiplier to restrict articulation of the deck section.

11. The patient support apparatus according to claim 1, wherein the biasing device further comprises a resiliently flexible biasing element coupled to the interface.

12. The patient support apparatus according to claim 11, wherein the actuator further comprises a housing coupled to the support frame with the housing rotatably supporting the torque multiplier.

13. The patient support apparatus according to claim 12, wherein the biasing element of the biasing device comprises a torsion spring having a first spring end and a second spring end with the first spring end coupled to the housing and with the second spring end coupled to the interface.

14. The patient support apparatus according to claim 1, wherein the deck section is arranged for articulation between the first position and the second position about an articulation axis.

15. The patient support apparatus according to claim 14, wherein the deck section comprises a deck coupler rotatably fixed to the support frame and supporting the deck section for rotation about the articulation axis.

16. The patient support apparatus according to claim 14, wherein the deck section is arranged to pivot about the articulation axis through an arc of at least 30 degrees between the first position and the second position.

17. The patient support apparatus according to claim 14, wherein the torque multiplier further comprises a link to transmit force between the biasing device and the deck section, the link having a first link end and a second link end with the first link end rotatably coupled to the deck section and with the second link end operably coupled to the interface such that the first link end is spaced from the second link end.

\* \* \* \* \*